US012186095B2

(12) United States Patent
Zealand et al.

(10) Patent No.: US 12,186,095 B2
(45) Date of Patent: Jan. 7, 2025

(54) INTELLIGENT CLOTHING FOR ENHANCED MOBILITY

(71) Applicant: Skip Innovations, Inc., San Francisco, CA (US)

(72) Inventors: Kathryn Jane Zealand, Palo Alto, CA (US); Elliott J. Rouse, Ann Arbor, MI (US)

(73) Assignee: Skip Innovations, Inc., San Francisco, CA (US)

( * ) Notice: Subject to any disclaimer, the term of this patent is extended or adjusted under 35 U.S.C. 154(b) by 1081 days.

(21) Appl. No.: 17/025,037

(22) Filed: Sep. 18, 2020

(65) Prior Publication Data

US 2021/0084997 A1 Mar. 25, 2021

Related U.S. Application Data

(60) Provisional application No. 62/903,119, filed on Sep. 20, 2019.

(51) Int. Cl.
*A61B 5/00* (2006.01)
*A41D 1/00* (2018.01)
(Continued)

(52) U.S. Cl.
CPC ............ *A61B 5/6804* (2013.01); *A41D 1/002* (2013.01); *G01P 13/00* (2013.01); *G06F 3/011* (2013.01); *G06V 10/82* (2022.01); *G06V 40/23* (2022.01); *A41D 2400/38* (2013.01); *A61H 2201/5058* (2013.01)

(58) Field of Classification Search
CPC .... A61B 5/6804; A61B 5/6812; G06V 10/70; G06V 10/82; G06V 40/20–28; A41D 1/002–005; A41D 2400/38; G01P 13/00; G06F 3/011; A61H 2201/1645–165; A61H 2201/5058–5094; A61H 3/00; A61H 3/007; A61F 5/01–0102; A61F 5/0106–0109; A61F 5/0123; A61F 5/0127–013
See application file for complete search history.

(56) References Cited

U.S. PATENT DOCUMENTS

2017/0028551 A1\* 2/2017 Hemken ................... B25J 9/163
2018/0092536 A1\* 4/2018 Sandler ................... G08C 17/00
(Continued)

*Primary Examiner* — Rachel T Sippel
(74) *Attorney, Agent, or Firm* — Mughal Gaudry & Franklin PC (57) ABSTRACT

Methods and systems for supporting and/or assisting users' movements include detecting, by one or more sensors integrated with a garment having two or more controllable regions, movement of a particular part of a user's body enclosed within the garment, measuring, by the one or more sensors, data that indicates the detected movement of the particular part of the user's body, determining, based on the measured data, an activity classification that indicates a future movement of the particular part of the user's body, identifying, based on the determined activity classification and by the one or more processors, a support configuration for the garment, and dynamically adjusting, by the one or more processors, at least one of an effective tension and an effective stiffness of at least one of the two or more controllable regions of the garment to provide the identified support configuration of the garment.

17 Claims, 3 Drawing Sheets

(51) Int. Cl.
  *G01P 13/00* (2006.01)
  *G06F 3/01* (2006.01)
  *G06V 10/82* (2022.01)
  *G06V 40/20* (2022.01)

(56) References Cited

U.S. PATENT DOCUMENTS

| | | | |
|---|---|---|---|
| 2019/0374161 A1* | 12/2019 | Ly | A61F 2/68 |
| 2020/0147384 A1* | 5/2020 | Caban | A61N 1/0484 |
| 2021/0007874 A1* | 1/2021 | Galiana Bujanda | A61F 5/028 |
| 2022/0296129 A1* | 9/2022 | Dodemont | A61B 5/053 |

* cited by examiner

INTELLIGENT CLOTHING FOR ENHANCED MOBILITY

CROSS-REFERENCE TO RELATED APPLICATION

This application claims the benefit of U.S. Provisional Application No. 62/903,119 on Sep. 20, 2019, the contents of which are incorporated by reference herein.

BACKGROUND

This specification relates to intelligent clothing that supports and enhances mobility. Supportive clothing is generally in the form of single-purpose braces that provide one level of stiffness or structure.

SUMMARY

Intelligent clothing can improve mobility for users with a variety of needs. Presently available devices that provide support for users include orthotics—such as braces for the upper limbs, lower limbs, or spine—which generally provide support for a single type of movement, and do not have variable stiffnesses or structure. Users who need support for a single joint or limb may be forced to use different braces for different activities. These braces are rigid, heavy, and uncomfortable, and are usually conspicuous. In many cases, assistive devices (devices that help a user move) available are for highly specialized purposes, including military support and devices for users with severe loss of musculoskeletal function, and are not for everyday consumer users.

Individual mobility is critical to maintaining independence and quality of life for an increasing portion of the population. Mobility support solutions are currently limited in application and are not suitable for consumer use; nor are they personalized or personalizable to meet the needs of individual users. Various needs are addressed separately, and there is no single solution that can be adapted to support an array of differing conditions, including improvement of a previously identified condition.

The proposed methods and systems provide adaptive support and assistance to users by performing intelligent dynamic adjustment of tension and stiffness in specific areas of fabric or by applying forces to non-stretch elements within a garment that is comfortable enough to be suitable for frequent, everyday usage. The methods include detecting movement of a particular part of a user's body enclosed within the garment, determining an activity classification for that movement, identifying a support configuration for the garment tailored to the activity classification, and dynamically adjusting a tension and/or a stiffness of one or more controllable regions of the garment or applying force to non-stretch fabric elements in the garment to provide customized support and assistance for the user and the activity the user is performing. This dynamic adjustment is calculated based on a mobility model tailored to a particular activity and specific user characteristics. User movement and usage data is collected and used to improve a specific mobility model for the user or to generally improve models for other users.

Machine learning models can be applied to the proposed methods to classify detected movement, personalize models to a particular user, and implement safety and prevention features. For example, machine learning models can be applied to the proposed methods to detect whether a person's condition is improving; the support configuration for the garment can then be adjusted to encourage further improvement and reduce reliance on the garment. In another example, machine learning models can be applied to the proposed methods to classify detected movement and improve predictions of the user's subsequent movements to prevent injury through unexpected movement support or lack of movement support.

The proposed methods can be implemented in the form of a garment that is worn by a user. The garment includes safety features that allow the garment to be used without the supervision of a medical health professional. For example, activity classification as applied to the dynamic adjustment of support configurations of the garment serves to prevent falls or detect fatigue, among other functions. The garment can be used in non-clinical situations to aid in everyday activities and generally improve a user's quality of life without fostering dependence on the garment.

In one general implementation, the proposed methods include detecting, by one or more sensors integrated with a garment having two or more controllable regions, movement of a particular part of a user's body enclosed within the garment. The methods include measuring, by the one or more sensors, data that indicates the detected movement of the particular part of the user's body. The methods include determining, based on the measured data and by one or more processors communicably connected to the sensors and integrated with the garment, an activity classification that indicates a future movement of the particular part of the user's body. The methods include identifying, based on the determined activity classification that indicates the future movement of the particular part of the user's body and by the one or more processors, a support configuration for the garment. The methods include dynamically adjusting, by the one or more processors, at least one of a tension and a stiffness of at least one of the two or more controllable regions of the garment or applying force to non-stretch fabric elements in the garment to provide the identified support configuration of the garment.

In some implementations, dynamically adjusting at least one of the effective tension and the effective stiffness of at least one of the two or more controllable regions of the garment, includes controlling one or more actuators based on the determined activity classification.

In some implementations, determining the activity classification includes inputting, to a machine learning model trained to classify detected movement into an activity, the measured data that indicates the detected movement.

In some implementations, the machine learning model is selected based on one or more physical movement characteristics of the user selected from among: a gait, an amount of energy expenditure, an impact force, or a range of motion.

In some implementations, the methods include recording, by the one or more sensors, data that indicates detected movement of the particular part of the user's body in response to the dynamic adjustment of at least one of the effective tension and the effective stiffness of at least one of the two or more controllable regions of the garment, and updating, by the one or more processors, the machine learning model.

In some implementations, the methods include actuating, by the one or more processors, at least one of the two or more controllable regions of the garment, by controlling one or more actuators to dynamically adjust the fit of the garment to the user.

In some implementations, the methods include performing a diagnostic function, by the one or more processors and based on the detected user's movement of the particular part of the user's body.

Systems for implementing the proposed method can be embodied in various form factors. In one general implementation, the system can be embodied in a wearable garment that includes two or more controllable regions of fabric, one or more sensors, and an electronic controller in communication with the two or more controllable regions of fabric and the one or more sensors. The sensors detect movement of a particular part of a user's body enclosed within the garment and measure data that indicates the detected movement of the particular part of the user's body. The electronic controller determines, based on the measured data, an activity classification that indicates a future movement of the particular part of the user's body, identifies, based on the determined activity classification that indicates the future movement of the particular part of the user's body, a support configuration for the garment, and dynamically adjusts at least one of a tension and a stiffness of at least one of the two or more controllable regions of the garment or by applying force to non-stretch elements in the garment to provide the identified support configuration of the garment.

The details of one or more implementations are set forth in the accompanying drawings and the description, below. Other potential features and advantages of the disclosure will be apparent from the description and drawings, and from the claims.

Like reference numbers and designations in the various drawings indicate like elements. The components shown here, their connections and relationships, and their functions, are meant to be examples only, and are not meant to limit the implementations described and/or claimed in this document.

DETAILED DESCRIPTION

Providing individualized, adaptive support and adaptive assistance to users increases mobility and therefore quality of life and independence for a growing population. In general, conventional mobility solutions are not automatically tailored for particular users and their needs, cannot easily be adjusted to support different activities, and do not take into account a user's movement intent. These methods typically only support a single type of movement or activity for a generic user's musculoskeletal structure, and are not based on a particular user's body structure or activity.

The proposed methods and systems perform movement monitoring of a user's limbs and allows for dynamic adjustment of the support configuration of the system in real-time while contemporaneously or near-contemporaneously collecting movement data and adjusting the support configuration based on the movement data as it is taken. The movement data can be used with statistical and/or machine learning models to analyze a user's movements and movement intent in response to the support configuration. In some implementations, the movement data can be used to map out musculoskeletal structure to personalize support configurations to a particular user.

For example, the proposed methods can include continuously providing, by the intelligent garment, support or assistance to a particular limb or joint of the user, collecting movement data, predicting a movement intent of the user, designing a customized support configuration for the movement intent of the user, and applying stimulation to the fabric of the intelligent garment to provide the designed support configuration. The intelligent garment can include moving and/or rigid components that allow the garment to provide the desired support or assistance. For example, the intelligent garment can include a motor that facilitates the configuration of the garment to provide the desired support or assistance to the particular limb or joint of the user.

The proposed methods and systems can be implemented automatically. For example, the system can automatically determine the movement intent of a user or the level of difficulty experienced by the user in performing the movement to tailor support configurations to the particular user's body.

Figure 1:
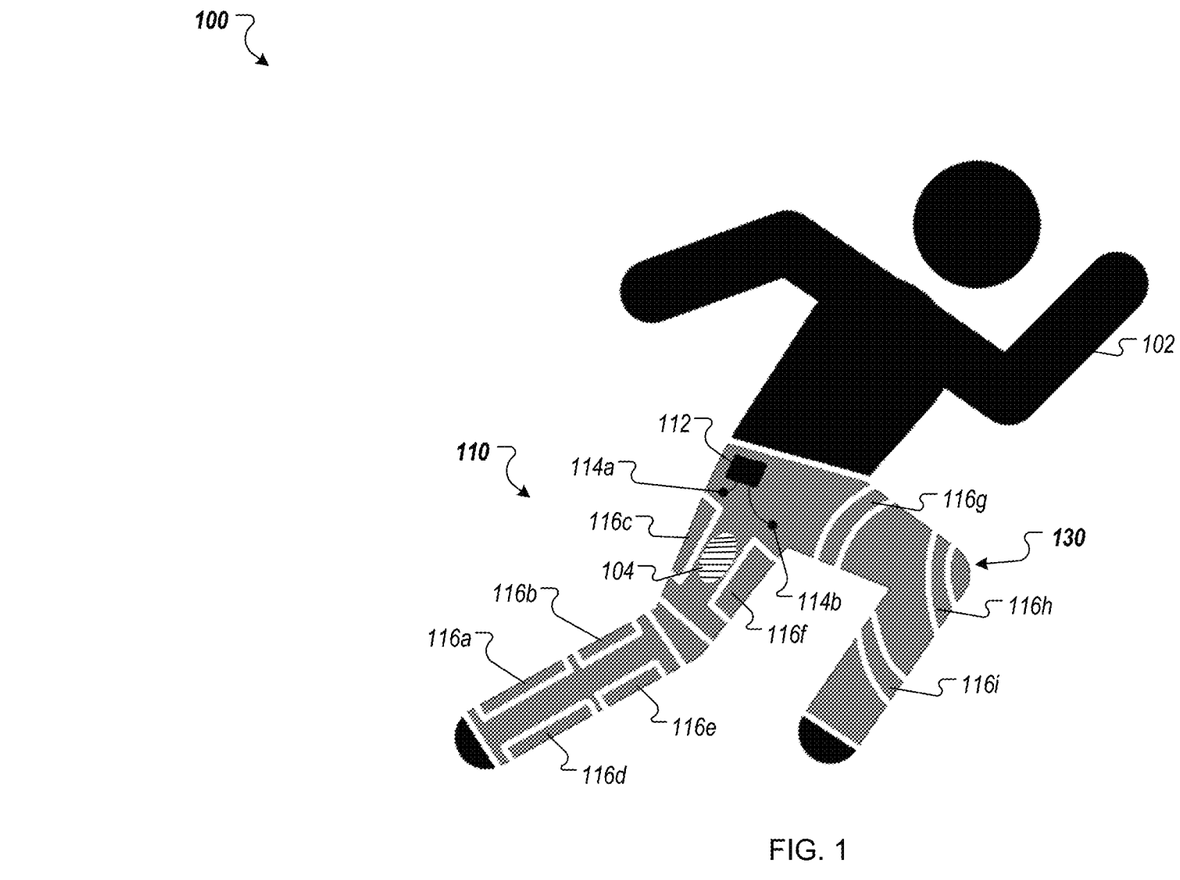
FIG. 1 is a diagram of an example configuration of an intelligent garment that enhances mobility.

FIG. 1 is a diagram of an example configuration 100 of an intelligent garment system 110. System 110 provides dynamically variable musculoskeletal support to a user. For example, system 110 can be used to support a user in a variety of movements by monitoring movement data and adjusting a support configuration of the system 110 based on a predicted movement intent of the user.

In this particular example, system 110 is in the form of a pair of pants 130 that can be worn on the user's lower body and provides support to the user's lower limbs, including the user's knees and ankles. In some implementations, system 110 can be in the form of a sock, a shoe, a shirt, a brace, an under-garment, or a full-body suit, among other forms of garments. For example, system 110 can be in the form of a shirt that can be worn on the user's upper body and provides support to the user's torso, including the user's back and spine.

In this particular example, system 110 can be used without an external power source. For example, system 110 can include an internal power source. The internal power source can be rechargeable and/or replaceable. For example, system 110 can include a replaceable, rechargeable battery pack that provides power to the components of system 110.

In some implementations, system 110 includes energy recycling systems, such as actuators that can recycle the energy generated when user 102 conducts movement activities, such as walking, running, climbing, and jumping, among other activities. For example, system 110 can use energy-recycling motors, or elastic actuators that stretch and recycle the energy stored when stretched to provide support when a user is reversing the action. System 110 can be used to assist activities such as squatting, such that energy is stored when a user is squatting and energy is released to support the user when the user is standing up. In some implementations, electrically driven actuators can be used to generate electricity when the actuators are returned to a steady state. For example, system 110 can be used to assist activities such as sitting down, such that energy is stored when a user is sitting down and energy is released to support the user when the user is getting up.

In some implementations, system 110 is environmentally sealed. For example, in some implementations, system 110 can be ingress protection (IP) rated against dust intrusion and full immersion for up to 30 minutes at depths between 15 cm and 1 m (i.e., IP67). In some implementations, a user can customize or select the degree to which system 110 is protected from the elements. For example, a user can choose for system 110 to be machine-washable.

In some implementations, system 110 is communicatively coupled to sensors 114, and uses data collected by sensors 114 and emitters 116 to determine an activity classification, optimal assistance profile, and/or a system configuration. In some implementations, system 110 is coupled to sensors 114 and emitters 116 through communication buses within environmentally sealed conduits. In some implementations, system 110 receives sensor data from sensors 114 and emitters 116 wirelessly through various wireless communications methods, such as RF, sonic transmission, electromagnetic induction, etc.

In some implementations, controller 112 is communicatively connected to other systems, such as sensors 114 and/or emitters 116 by, for example, through conductive threads linking sensors 114 and/or emitters 116 to controller 112 and/or the external power source.

User 102 is a human user of intelligent garment system 110.

A particular joint, limb, muscle, or muscle group within user 102 can be targeted. This target area 104 can be, for example, a specific group of muscles, such as the left hamstring, used in a particular movement activity, such as when user 102 is running. In some implementations, target area 104 can be automatically selected based on movement data. For example, system 110 can adjust the targeted area within user 102 based on detected movement activity and intent. In some implementations, target area 104 can be selected manually based on a target movement activity or user support goal. In this particular example, target area 104 is a muscle group of user 102's leg, which has been automatically selected for targeted support based on the detected stride of user 102.

Intelligent garment system 110 is shown to include a controller 112, sensors 114*a* and 114*b* (collectively referred to as sensors 114), and emitters 116*a*, 116*b*, 116*c*, 116*d*, 116*e*, 116*f*, 116*g*, 116*h*, and 116*i* (collectively referred to as emitters 116). System 110 is configured to provide dynamically adaptive support for user movement activities through an intelligent garment system.

System 110 allows contemporaneous or near-contemporaneous detection and classification of user movement and dynamic support of the movement, facilitating a closed loop system that is able to dynamically support a target area 104 in real time and make adjustments to the support and assistance configuration of the intelligent garment system based on the detected data. Detection and support may occur with very little delay between; for example, detection and support signals can occur within 200 ms of each other to enable the closed loop system. Detection and support signals can be multiplexed.

Sensors 114 detect movement activity of user 102's target area 104. Detection can be done using electrical, optical, and/or magnetic techniques by sensors such as accelerometers, gyroscopes, magnetometers, inertial measurement units (IMUs), GPS, electromyography (EMG), mechanomyography (MMG), visual sensors, depth sensors, and/or encoders, among other types of detection techniques. In this particular implementation, sensors 114 are IMUs. Sensors 114 can include temperature sensors, infrared sensors, light sensors, heart rate sensors, and blood pressure monitors, among other types of sensors. In addition to detecting activity of target area 104 of user 102, sensors 114 can collect and/or record the activity data and provide the activity data to controller 112.

Sensors 114 can perform optical detection such that detection does not interfere with the frequencies generated by emitters 116. For example, sensors 114 can perform near-infrared spectroscopy (NIRS) or ballistic optical imaging through techniques such as coherence gated imaging, collimation, wavefront propagation, and polarization to determine time of flight of particular photons. Additionally, sensors 114 can collect biometric data associated with user 102. For example, sensors 114 can detect the heart rate, eye movement, and respiratory rate, among other biometric data of user 102.

Sensors 114 provide the user's collected movement and activity data and other data associated with user 102 to controller 112.

Emitters 116 generate one or more electric fields at surrounding panels of a garment 130 to around a target area 104 within user 102. System 110 includes multiple emitters 116, each of which can actuate a portion of garment 130 to apply force(s) or torque(s) to support or assist the limb or joint of a user. In some implementations, actuation of the garment 130 can, for example, effect a particular stiffness and structure of a portion of garment 130. Emitters 116 can be, for example, electrodes. Emitters 116 can be powered by direct current or alternating current. Emitters 116 can be identical to each other. In some implementations, emitters 116 can include emitters made of different materials.

In some implementations, sensors 114 can include emitters that emit electric fields and detect movement of target area 104 or user 102. For example, emitters 116 can include one or more of sensors 114. In some implementations, emitters 116 include each of sensors 114; the same set of emitters can perform the support and detection of user movement in response to the stimulation. In some implementations, one subset of emitters may be dedicated to creating the necessary support configuration of garment 130—i.e., fabric control—and another subset dedicated to detection. In some implementations, the garment control system, i.e., emitters 116, and the detection system, i.e., sensors 114, are electromagnetically or physically shielded and/or separated from each other such that fields from one system do not interfere with fields from the other system. In some implementations, system 110 allows for contemporaneous or near-contemporaneous fabric control and measurement through, for example, the use of high performance filters that allow for high frequency control signals at a high amplitude during low noise detection.

In some implementations, system 110 uses emitters 116 to control a motor that applies force to non-stretch fabric elements in the garment. For example, emitters 116 can be controlled to apply a field that actuates a motor to pull on a non-stretch fabric element within the garment to apply force to the target area 104 of user 102. In some implementations, emitters 116 are actuators that separately actuate to apply force to elements within the garment surrounding the target area 104 of user 102. For example, each of emitters 116 can be a separate motor that pulls or releases a non-stretch fabric element within the garment to apply force to the target area 104 of user 102.

Controller 112 includes one or more computer processors that control the operation of various components of system 110, including sensors 114 and emitters 116 and components external to system 110, including systems that are integrated with system 110.

Controller 112 generates control signals for system 110 locally. The one or more computer processors of controller 112 continually and automatically determine control signals for the system 110 without communicating with a remote processing system. For example, controller 112 can receive user movement feedback data from sensors 114 in response to support from emitters 116 and process the data to determine control signals and generate control signals for emitters 116 to alter or maintain one or more fields generated by emitters 116 within the target area 104 of user 102.

Controller 112 controls sensors 114 to collect and/or record data associated with movement of user 102 and target area 104. For example, sensors 114 can collect and/or record data associated with movement of target area 104. In some implementations, controller 112 can control sensors 114 to detect the response of target area 104 of user 102 to stimulation generated by emitters 116. Sensors 114 can also measure movement and activity through optical, electrical, and magnetic techniques, among other detection techniques.

Controller 112 is communicatively connected to sensors 114. In some implementations, controller 112 is connected to sensors 114 through communications buses with sealed conduits that protect against solid particles and liquid ingress. In some implementations, controller 112 transmits control signals to components of system 110 wirelessly through various wireless communications methods, such as RF, sonic transmission, electromagnetic induction, etc.

Controller 112 can receive feedback from sensors 114. Controller 112 can use the feedback from sensors 114 to adjust subsequent control signals to system 110. The feedback, or user 102's target area 104's response to stimulation generated by emitters 116 can have frequencies on the order of tens of Hz and voltages on the order of $\mu V$. T 104's response to stimulation generated by emitters 116 can be used to dynamically adjust the stimulation, creating a continuous, closed loop system that is customized for user 102.

Controller 112 can be communicatively connected to sensors other than sensors 114, such as sensors external to the system 110, and uses the data collected by sensors external to the system 110 in addition to the sensors 114 to generate control signals for the system 110. For example, controller 112 can be communicatively connected to biometric sensors, such as heart rate sensors or eye movement sensors that are external to the system 110.

In some implementations, controller 112 receives environmental data regarding a user's surroundings and uses this environmental data as input to the models. For example, controller 112 can receive video data that shows the user's surroundings. Controller 112 can use the video data to determine characteristics of the user's surroundings, such as whether the user is inside of a building, whether the user is at a track for running, or whether the user is dressed for a particular type of sport, among other factors. Controller 112 can receive, for example, floor plans of the user's surrounding area. For example, controller 112 can determine, from received floor plans, that a user is approaching a set of stairs, and that the user will likely attempt to climb the stairs.

Controller 112 can use received information to determine the information needed to generate a prediction using the models. For example, controller 112 can determine, based on the user's GPS location, which floor plans are applicable to the area within which the user is moving. Controller 112 can then retrieve appropriate floor plans to be used as input to the models.

Controller 112 can accept input other than IMU data from the sensors 114. The input can include sensor data from sensors separate from system 110, such as temperature sensors, light sensors, heart rate sensors, and blood pressure monitors, among other types of sensors. In some implementations, the input can include user input. In some implementations, and subject to safety restrictions, a subject can adjust the operation of the system 110 based on the user's comfort level. For example, the subject can provide direct input to the controller 112 through a user interface. In some implementations, controller 112 receives sensor information regarding the condition of a user. For example, sensors monitoring the heart rate, respiratory rate, temperature, blood pressure, etc., of a subject can provide this information to controller 112. Controller 112 can use this sensor data to automatically control system 110 to alter or maintain the support provided to target area 104 of user 102.

Controller 112 uses data collected by sensors 114 and sources separate from system 110 to reconstruct characteristics of activity detected in response to support configurations from emitters 116.

Controller 112 controls the selection of which of emitters 116 to activate for a particular support configuration. Controller 112 controls the voltage, frequency, and phase of electric fields generated by emitters 116 to produce a particular support configuration of garment 130. In some implementations, controller 112 uses emitters 116 to control the stiffness and structure of particular panels of garment 130 to create a particular support configuration. In some implementations, controller 112 turns on various combinations of emitters 116, which may have differing operational parameters (e.g., voltage, frequency, phase) to create various support and assistance configurations of garment 130.

In some implementations, controller 112 transmits collected movement data from sensors 114 and other sensors and provides the data to a remote system. The remote system can conduct long-term processing of the model for the particular user. For example, the remote system can update the model for the particular user based on the movement data and feedback received from sensors 114 and other sensors. The remote system can perform long-term modelling of a particular user's movements to perform, for example, diagnostic functions.

Controller 112 selects one or more of emitters 116 to activate and controls emitters 116 to control the support configuration of an intelligent garment 130 based on detection data from sensors 114 and stimulation parameters for user 102. In some implementations, controller 112 selects particular emitters based on the position of the target area. For example, controller 112 can select opposing emitters closest to the target area 104 of user 102. In some implementations, controller 112 selects particular emitters based on the support configuration for the garment 130. For example, controller 112 can select emitters 116 capable of producing a particular voltage or frequency of electric field nearest to the target area 104. In another example, controller 112 can select particular emitters 116 that actuate to apply force to particular elements of the garment to apply force to the target area 104.

The elements of the garment can include, for example, non-stretch fabric elements that are comfortable enough to be worn by user 102 on a regular basis, but that can provide support to user 102 when actuation is applied. For example, the elements can be non-stretch fabric panels that are pulled by emitters 116, that are motors in this example, in order to provide support by effectively creating tension and/or stiffness at the target area 104 using elements of the garment.

Controller 112 operates multiple emitters 116 to generate electric fields at the target area 104 of user 104. Controller 112 operates multiple emitters 116 to generate electric fields using direct current or alternating current. Controller 112 can operate multiple emitters 116 to create interfering electric fields that interfere to produce fields of differing frequencies and voltage. For example, controller 112 can operate two opposing emitters 116 (e.g., emitters 116c and 116f) to generate two electric fields having frequencies on the order of kHz that interfere to produce an interfering electric field having a frequency on the order of Hz and produce a particular support configuration of garment 130. Controller 112 can control operational parameters of emitters 116 to generate electric fields that interfere to create an interfering field having a particular beat frequency. In some implementations, the beat frequency of the interfering field can be less than 100 Hz. The voltages of the electric fields generated by emitters 116 are on the order of 0.5 to a few Volts.

In some implementations, controller 112 can communicate with a remote server to receive new control signals. For example, controller 112 can transmit feedback from sensors 114 to the remote server, and the remote server can receive the feedback, process the data, and generate updated control signals for the system 110 and other components.

System 110 can receive input from user 102 and automatically determine a target area 104 and control emitters 116 to produce a particular support configuration for fabric around target area 104. For example, controller 112 can determine, based on collected feedback information from user 102's body, an updated support configuration for the fabric around target area 104.

A support configuration identifies a set of controllable regions within garment 130 that can be adjusted to support a target area 104 of user 102, and an extent and way in which the regions are to be adjusted. For example, a support configuration can identify a set of emitters 116 that, in this particular example, are motors, that can actuate to pull or release particular non-stretch fabric elements integrated within garment 130. The support configuration can specify, for example, an amount that the elements are to be pulled and the force with which the elements are to be held in place, among other parameters, in order to achieve a particular level and type of support appropriate for the particular target area 104.

System 110 performs activity detection and classification to uniquely tailor support for a particular user 102. In some implementations, the system 110 can start with a baseline map of musculoskeletal structure and functionality and dynamically adjust support for target area 104 based on activity feedback detected by sensors 114. In some implementations, system 110 can start with provisionally tailored maps that are generally applicable to a subset of users 102 having a set of characteristics in common and dynamically adjust support to target area 104 of user 102's body based on activity feedback detected by sensors 114.

System 110 is generally used for non-clinical applications. For example, controller 112 can control emitters 116 such that the amount of support provided to user 102 is lower than a therapeutic threshold. In some implementations, controller 112 can be used to support user 102 such that improvement in a gait or a range of motion is improved. For example, controller 112 can be used to support a target area 104 of user 102 to improve the symptoms of a particular muscular condition. In some implementations, controller 112 can be used to support a target area 104 of user 102 to reduce fatigue.

System 110 includes safety functions that allow a subject to use the system 112 without the supervision of a medical professional. In some implementations, system 110 can be used by a subject for non-clinical applications in settings other than under the supervision of a medical professional. For example, system 110 can implement limits on the amount of time that system 110 can be used or enforce a maximum amount of support that can be provided by system 110. System 110 can perform a decoupling of an actuator of garment 130 from garment 130 such that, for example, an actuator of garment 130 is mechanically decoupled from garment 130 when system 110 is off or when there is an error in system 110.

In some implementations, system 110 cannot be activated by a subject without the supervision of a medical professional, or cannot be activated by a user at all. For example, system 110 may require credentials from a medical professional prior to use. In some implementations, only a healthcare professional trusted by user 102, such as a doctor, physiotherapist, or trained rehabilitation therapist, among other professionals, can turn on system 110 remotely or at their office. In some implementations, system 110 can receive configuration information from a medical professional. For example, system 110 can receive configuration information that has been generated by a medical professional for the particular user based on the user's collected movement and activity data.

In some implementations, system 110 can uniquely identify a user 102, and may only be used by the user 102. For example, system 110 can be locked to particular subjects and may not be turned on or activated by any other users.

System 110 can limit the range of support, stiffness, and structure effected by emitters 116 to prevent delivery of harmful patterns of stimulation. For example, system 110 can detect, over a period of time, degradation in balance of a user 102's movements, and generate a notification that user 102 is now classified as high-risk for an injury. System 110 can, for example, generate a notification that triggers an occupational health assessment or alerts user 102 to their degradation in movement. System 110 can detect, in another example, that a user 102's running gait is causing user 102 long-term damage to their lower limb joints. System 110 can then preventatively actuate garment 130 to correct user 102's running gait.

Controller 112 can use statistical and/or machine learning models which accept sensor data collected by sensors 114 and/or other sensors as inputs. The machine learning models may use any of a variety of models such as decision trees, linear regression models, logistic regression models, neural networks, classifiers, support vector machines, inductive logic programming, ensembles of models (e.g., using techniques such as bagging, boosting, random forests, etc.), genetic algorithms, Bayesian networks, etc., and can be trained using a variety of approaches, such as deep learning, association rules, inductive logic, clustering, maximum entropy classification, learning classification, etc. In some examples, the machine learning models may use supervised learning. In some examples, the machine learning models use unsupervised learning.

Figure 2:
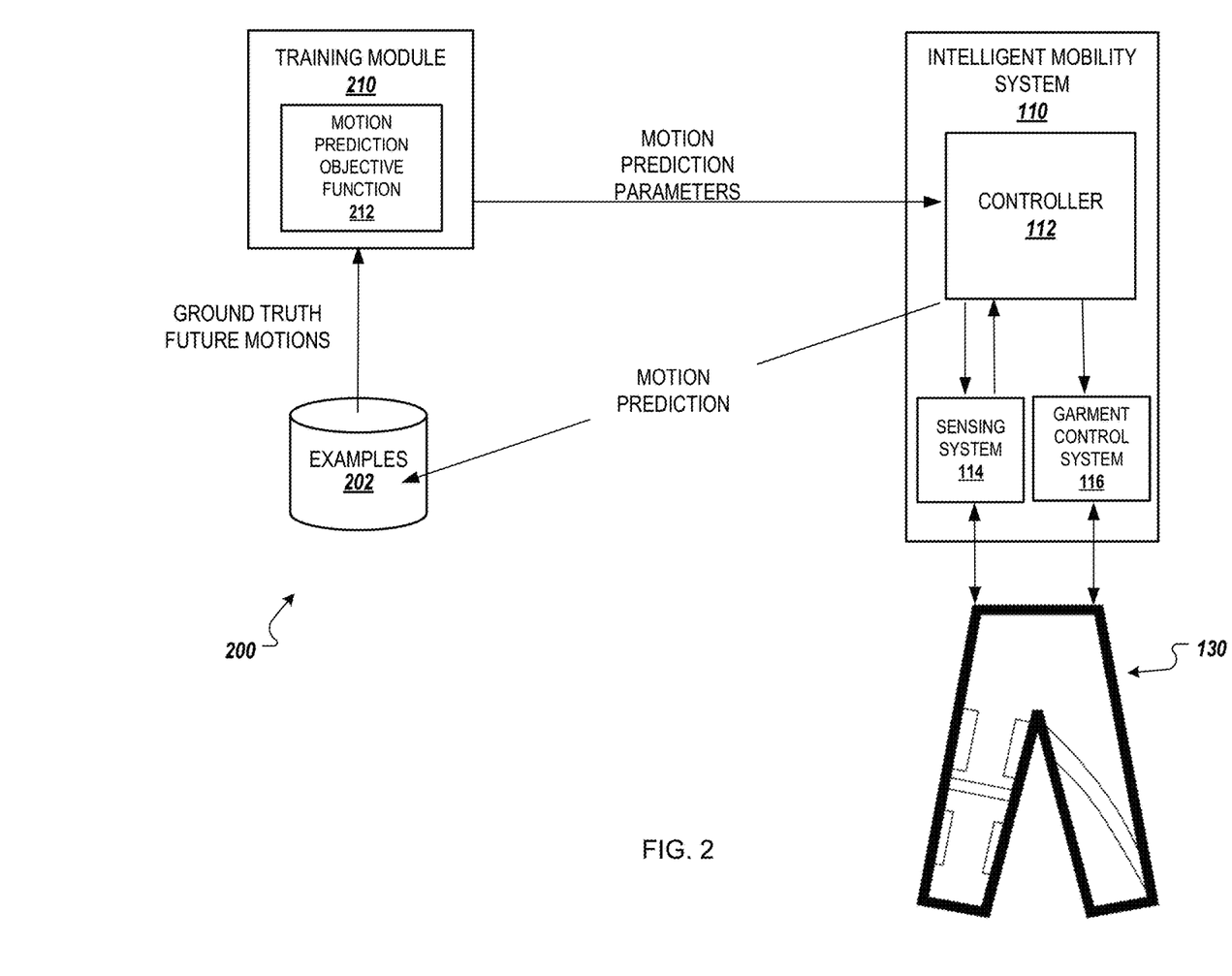
FIG. 2 is a diagram of an example machine learning process for activity classification and support configuration.

FIG. 2 is a diagram of an example block diagram of a system 200 for training an intelligent garment system. For example, system 200 can be used to train intelligent garment system 110 as described with respect to FIG. 1.

As described above with respect to FIG. 1, system 110 includes a controller 112 that classifies activity detected by a sensing system and determines electrical stimulation patterns for a garment 130 to produce a particular support configuration for a user 102. For example, controller 112 classifies activity detected by a sensor system (e.g., sensors 114) and determines stimulation parameters for a garment control system (e.g., emitters 116). Activity classification includes predicting a future motion of user 102 based on the detected activity of user 102. Activity classification can include identifying the location and intensity of an activity.

Examples 202 are provided to training module 210 as input to train a motion prediction model. Examples 202 can be positive examples (i.e., examples of correctly determined future motions) or negative examples (i.e., examples of incorrectly determined future motions).

Examples 202 include the ground truth future motions, or a future motion defined, or confirmed, as the correct future motion. Examples 202 include sensor information such as baseline activity patterns for a particular user. For example, examples 202 can include movement data for user 102 generated through activity detection performed by sensors 114 or sensors external to system 110 as described above.

The ground truth indicates the actual, correct future motion indicated by the activity. For example, a ground truth future motion can be generated and provided to training module 210 as an example 202 by detecting an activity, classifying the activity, and confirming that the activity classification is correct. In some implementations, a human can manually verify the future motion. The future motion can be automatically detected and labelled by pulling data from a data storage medium that contains verified future motions.

The ground truth future motion can be correlated with particular inputs of examples 202 such that the inputs are labelled with the ground truth future motion. With ground truth labels, training module 210 can use examples 202 and the labels to verify model outputs of a motion predictor and continue to train the predictor to improve forward modelling of movement activity through the use of detection data from sensors 114 to classify activities and predict movements in response to support configurations.

The sensor information guides the training module 210 to train the classifier to categorize movement data and predict future movements. The training module 210 can associate patterns of movements of user 102's body with a future movement to map out movement ranges and activities. Inverse modelling of movement activity can be conducted by using measured responses to approximate support configurations that could produce the measured responses. The training module 210 can train the classifier to learn how to map multiple raw sensor inputs to various types of movements and activity classification based on a structurally correlated map. Thus, the classifier would not need additional prior knowledge during the testing phase because the classifier is able to map sensor inputs to respective areas of user 102's body and predict future movements using the correlated map.

Training module 210 trains a motion prediction model to perform motion prediction. For example, training module 110 can train controller 112 to recognize movement activity based on inputs from sensors of user 102's body. Training module 210 refines controller 112's motion prediction model using movement data collected by sensors 114 for a particular user 102. Training module 210 allows controller 112 to output complex results, such as a predicted movement intent instead of, or in addition to, simple future movements.

A movement intent suggests an intent for future movements. For example, a movement intent can suggest that a user will continue to perform their current movement activity. A movement intent can suggest that a user intends to transition to a different activity. For example, a movement intent can suggest that a user will transition from running to walking. Controller 112 uses these movement intents to determine an appropriate support configuration for garment 130 such that user 102 will receive the desired support.

Training module 210 trains controller 112 using a motion prediction objective function 212. Training module 110 uses motion prediction objective function 212 to train controller to predict a future motion. Activity classification objective function 212 can account for variables such as a predicted location, a predicted amplitude, a predicted frequency, and/or a predicted phase of a detected activity.

Training module 210 can train controller 112 manually or the process could be automated. For example, if an existing representation of a particular area of user 102's musculoskeletal structure is available, the system can receive sensor data indicating movement activity in response to a known support configuration to identify the ground truth area 104 within user 102's body. A human can also manually verify the support and/or assistive configurations.

Training module 210 uses the objective function 112 and examples 202 labelled with the ground truth future motions to train controller 112 to learn what is important for the model. Training module 210 allows controller 112 to learn by changing the weights applied to different variables to emphasize or deemphasize the importance of the variable within the model. By changing the weights applied to variables within the model, training module 210 allows the model to learn which types of information (e.g., which sensor inputs, what locations, etc.) should be more heavily weighted to produce a more accurate motion predictor.

The examples and variables can be weighted based on, for example, feedback from controller 112. For example, if controller 112 collects movement and/or activity data that indicates that a user achieving an objective function (e.g., activity level, gait, etc.) is being supported and/or assisted by a particular supportive/assistive configuration of garment 130, then controller 112 can weigh the applied configuration more heavily than other configurations that do not achieve the objective function.

Training module 210 uses machine learning techniques to train controller 112, and can include, for example, a neural network that utilizes motion prediction objective function 212 to produce parameters used in the motion prediction model. These parameters can be prediction parameters that define particular values of a model used by controller 112.

In some implementations, controller 112 uses an objective function to achieve the specified objective. The objective can be specified by user 102.

In some implementations, the objective of controller 112 is to provide enough support to user 102 such that user 102 is not fatigued. Controller 112 can modulate the support provided to user 102 to reduce the risk of dependency on system 110 while providing enough support to user 102 to improve mobility. In some implementations, the objective of controller 112 is to provide assistance to user 102 such that user 102 can perform a desired motion.

System 110 can conform to a user's musculoskeletal structure when the user puts on intelligent garment system 110. For example, if user 102 has a slight difference in muscle development between their legs, system 110 can conform to user 102's legs to best support each leg.

Controller 112 classifies movement activity based on data collected by sensors 114. Controller 112 performs forward modelling of movement activity and inverse modelling of movement activity, given base, reasonable assumptions regarding the support provided to a target area 104 of user 102.

Controller 112 can include a state machine and a low-level controller. In some implementations, the state machine receives data from a motion prediction model and can maintain and change states in response to external inputs. The state machine can be, for example, a finite state machine or an infinite state machine. In some implementations, the state machine provides state information to a low-level controller that generates and provides control signals to garment control system 116. Controller 112 can also include an assistance optimizer that receives data and feedback from sensing system 114 and garment control system 116 and provides input to the low-level controller.

Forward modelling allows controller 112 to determine supportive and/or assistive configurations that will produce a particular reaction from a target 104 portion of user 102. For example, controller 112 can receive a specified objective (e.g., a reduced amount of energy required to perform a movement activity) and design stimulation field patterns for emitter 116 to actuate garment 130 and produce a supportive and/or assistive configuration of garment 130. Controller 112 can then control two or more emitters 116 to apply electrical fields to fabric panels of garment 130 to achieve the specified objective.

Inverse modelling allows controller 112 to estimate the most likely relationship between the detected response movement data and particular areas of user 102. For example, controller 112 can receive movement activity data from sensors 114 and reconstruct, using a motion prediction model, the location, intensity, expended energy, etc. of the activity. Controller 112 can then dynamically alter the existing mobility model of user 102's body based on the reconstruction.

Controller 112 can use various types of models, including general models that can be used for all patients and customized models that can be used for particular subsets of patients sharing a set of characteristics, and can dynamically adjust the models based on the musculoskeletal structure of a particular user 102 or based on detected activity, such as a user's detected health or an automatically determined optimized movement. For example, the classifier can use a base network for users and then tailor the model to each user. The movement activity can be detected by sensors 114 contemporaneously or near-contemporaneously with the support provided by emitters 116. In some implementations, the movement activity can be detected through techniques performed by systems external to system 110, such as functional magnetic resonance imaging (fMRI) or diffusion tensor imaging (DTI).

System 110 can detect and classify a vast number of activities. System 110 is also able to detect the transitions between classified activities in a small amount of time in order to dynamically adjust the support provided to user 102.

In addition to classifying activities of user 102 based on movement data, controller 112 of system 110 solves an optimization problem to determine the appropriate tensions, stiffnesses, and/or structures to implement in fabric 130. This optimization problem can be represented, for example, by an objective function that defines the objective of system 110. In some implementations, system 110 can use machine learning to determine an objective function for a particular user based on subjective feedback from the user. The objective function can be simple and provide general support. For example, an objective function of a user 102 can include a function of user 102's input mechanical energy and user 102's deviations from their own natural, unfatigued gait (e.g., determined based on user 102's ankle angle). The objective function can be complex and provide dynamically tailored support and/or assistance in a user's movements. For example, the objective function for a user 102 can be a function of user 102's perceived pain, user 102's endurance (e.g., difference from a non-fatigued gait and the present gait), user 102's perceived effect (e.g., determined through metabolic cost and heartrate), the variations from a "healthy" gait for a user of user 102's given age and physiology, an injury prevention factor, user 102's stability (e.g., difference between user 102's line of motion vs. a "healthy" line of motion), user 102's speed of motion, and user 102's perceived comfort (e.g., the deviation of user 102's gait from user 102's unassisted gait, because abrupt changes can cause shear stress on the user's skin).

As system 110 collects movement data while user 102 moves, system 110 anonymizes the data and provides the data to a central database that stores and analyzes the collected data to improve general mobility models and allow system 110 to provide more individualized strategies for each user 102.

System 110 can, for example, utilize a general profile for a user having a particular age, height, etc. System 110 can generalize support configurations across users who are predicted to have similar support needs and musculoskeletal structures. In some implementations, system 110 accepts input, from a user, of profile information such as the user's age, height, weight, etc.

System 110 can estimate a user's age from movement data. For example, system 110 can determine, based on data from sensors 114, a user's walking speed and gait, and use these parameters to predict a user's age and height. In some implementations, system 110 can determine, for example, whether a user has a healthy gait, or whether the user has non-optimal movement. For example, if a user has a problem with walking with a limp, system 110 can identify the limp and a predicted support configuration that reduces the severity of the limp.

System 110 can utilize, for example, a "shoe size" model that is individualized to a certain extent. For example, system 110 can use general profiles for older people, for taller people, for people having scoliosis, etc. System 110 can alter, for example, profiles based on a user's characteristics, such as predicting larger, slower strides for a taller person.

Each model can be individualized. For example, each model can be created from a generic model by altering model parameters based on the characteristics for each user determined from the collected data. Each model can vary for a particular user over long periods of time and short periods of time. For example, system 110 can track how fatigued a user is and apply a more assistive profile when the user is more fatigued. In some implementations, each model can also be created from a model that has been individualized using a general profile and further altered for each user. For example, a model can be created by altering model parameters based on the characteristics for each user determined from the collected data.

Models can be individualized for therapeutic purposes as well. For example, controller 112 can individualize a model to reduce the stress on a target area 104 of user 102, such as their knee. System 110 can update each model based on movement response information from each user 102 to improve the models and to update the determined support configuration for user 102.

System 110 is a closed loop system that receives response information and dynamically updates mobility models based on this response information. The mobility models are used to determine, for example, the activity being performed by a user and their movement intent for short term support configuration updates.

In general, injury can result when system 110 causes the user to perform something they did not intend. Injury can also be caused when a user wants to do something and the user is fighting system 110 against what the models have predicted as the user's intended next action.

The models are trained to prioritize safety through prophylactic and reactive measures. For example, the models can operate to prevent situations in which injury can occur. The models can use conservative predictions of a user's future motion, for example, to increase a threshold amount of change in movement data to qualify as an intent to transition activities to prevent aggressive support for activity transitions that could injure a user. For example, in order to prevent injury by supporting a user to transition from walking to climbing steps, controller 112 can increase a threshold amount of change detected in movement data to qualify as an intention to transition from walking to climbing steps so that system 110 does not force user 102 to begin climbing steps when they are simply walking.

In some implementations, the models can use aggressive predictions of a user's activity classification and movement intent, for example, to decrease a threshold amount of change in movement data to qualify as an intent to transition activities to prevent system 110 from providing support for a previous activity and force a user to act against system 110, which could cause injury. For example, in order to prevent injury by supporting a user to slow down to a walk instead of continuing to run, controller 112 can decrease a threshold amount of change detected in movement data to qualify as an intention to transition from running to walking so that system 110 does not force user 102 to continue running instead of beginning their cool down by walking.

The models can operate to detect early signs and mitigate the effects of injurious activity. For example, the models can analyze movement data and determine that a user is about to fall. The models can then determine a support configuration to prevent the fall. System 110 can send an alert to the user to warn them, in case the user's attention is not fully on the task.

In some implementations, if the fall is inevitable, the models can determine a support configuration that mitigates the effects of the fall, and/or system 110 can perform an action that assists the user. For example, system 110 can send alerts to a third party, such as emergency responders, a designated contact, etc.

In certain implementations, the intelligent garment system is a highly tailored garment such that system 100 is close-fitting to a user's body. In some implementations, system 100 can receive user measurements and system 100 can determine a configuration of system 100 that is best fitted to the user's body. For example, system 100 can be custom-fit to the user using a 3D scan of the user's body. In some implementations, system 100 can actuate garment 130 to adjust compression levels of portions of garment 130 to produce a "self-tightening" effect and dynamically adjust the fit of garment 130 to the user's body.

Figure 3:
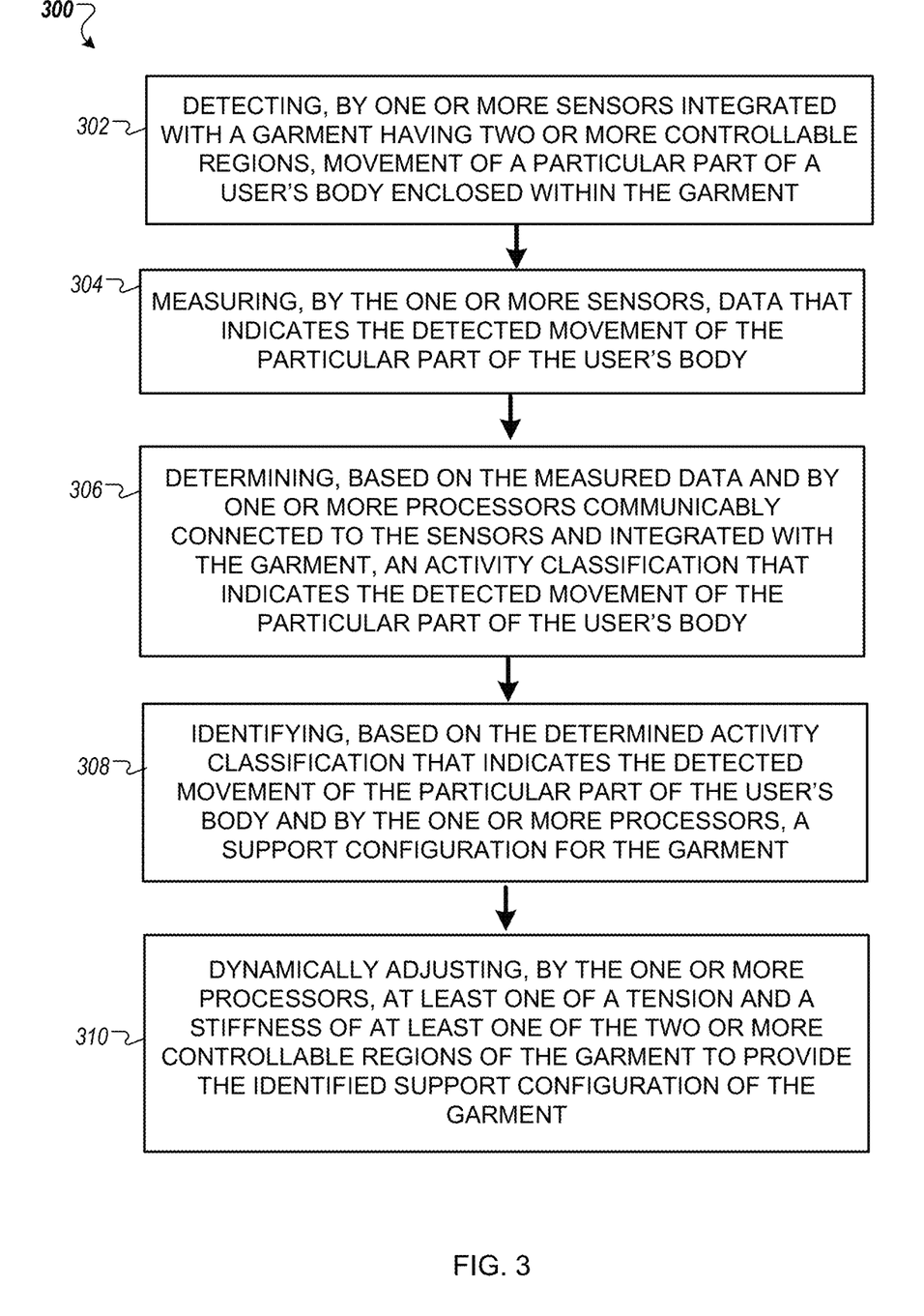
FIG. 3 is a flow chart of an example process of an intelligent garment determining and implementing a support configuration.

FIG. 3 is a flow chart of an example process 300 of dynamically adjusting a support configuration of a garment for a particular user. Process 300 can be implemented by intelligent garment systems such as system 110 as described above with respect to FIGS. 1 and 2. In this particular example, process 300 is described with respect to system 110 in the form of a pair of pants that can be worn and used by a user without the supervision of a medical professional. Briefly, according to an example, the process 300 begins with detecting, by one or more sensors integrated with a garment having two or more controllable regions, movement of a particular part of a user's body enclosed within the garment (302). For example, system 110 can detect, using sensors 114 integrated with garment 130 that has controllable regions, such as non-stretch fabric elements controlled by emitters 116, movement of a part of user 102's body within the garment 130. The part can be, for example, target region 104 of user 102's body that is enclosed within garment 130, such as user 102's knee The process 300 continues with measuring, by the one or more sensors, data that indicates the detected movement of the particular part of the user's body (304). System 110 can measure, using sensors 114, data that indicates the detected movement of the particular part 104 of user 102's body.

The process 300 continues with determining, based on the measured data and by one or more processors communicably connected to the sensors and integrated with the garment, an activity classification that indicates the detected movement of the particular part of the user's body (306). System 110 can determine, using controller 112 and based on the measured data, an activity classification for the detected movement that indicates the detected movement and target area 104 of user 102's body. For example, system 110 can determine, using controller 112 and based on the measured data, that user 102 is walking up a flight of stairs and that the target area 104, user 102's knee, is in need of support.

The process 300 continues with identifying, based on the determined activity classification that indicates the detected movement of the particular part of the user's body and by the one or more processors, a support configuration for the garment (308). System 110 can identify, by controller 112 and based on the determined activity classification that indicates movement of target area 104 of user 102's body, a support configuration for garment 130. For example, system 110 can identify, by controller 112 and based on determining that user 102 is walking up a flight of stairs and needs support in their knee, a particular configuration created by actuating a set of emitters 116 to pull on non-stretch fabric elements within garment 130 to create a support configuration.

The process 300 concludes with dynamically adjusting, by the one or more processors, at least one of a tension and a stiffness of at least one of the two or more controllable regions of the garment to provide the identified support configuration of the garment (310). System 110 can, for example, dynamically adjust, using controller 112 and emitters 116, the stiffness of two controllable regions of garment 130 to provide the identified support configuration of system 110 by actuating to pull on non-stretch fabric elements within garment 130 that surround the user 102's knee.

What is claimed is:
1. A method, comprising:
   detecting, by one or more sensors integrated with a garment having two or more controllable regions, movement of a particular body part of a user of a plurality of users, wherein the particular body part is a part of the user's body enclosed within the garment;
   measuring, by the one or more sensors, data that indicates the detected movement of the particular body part of the user's body;
   determining, based on the measured data and by one or more processors communicably connected to the sensors and integrated with the garment, an activity classification that indicates a future movement of the particular body part of the user's body, wherein:
   the activity classification comprises inputting, to a machine learning model trained to classify the detected movement into an activity type, the measured data, and the machine learning model is trained specifically for the user and movement characteristics of the user that includes at least one of: an amount of energy expenditure, an impact force, or a range of motion;
identifying, based on the determined activity classification that indicates the future movement of the particular body part of the user's body and by the one or more processors, a support configuration of the garment; and
dynamically adjusting, by the one or more processors, at least one of a tension and a stiffness of at least one of the two or more controllable regions of the garment to provide the identified support configuration of the garment.

2. The method of claim 1, wherein dynamically adjusting at least one of the tension and the stiffness of at least one of the two or more controllable regions of the garment, comprises controlling one or more actuators based on the determined activity classification.

3. The method of claim 1, wherein determining the activity classification comprises inputting, to the machine learning model trained to classify detected movement into an activity, the measured data that indicates the detected movement.

4. The method of claim 3, further comprising:
recording, by the one or more sensors, data that indicates detected movement of the particular part of the user's body in response to the dynamic adjustment of at least one of the tension and the stiffness of at least one of the two or more controllable regions of the garment; and
updating, by the one or more processors and based on the recorded data, the machine learning model.

5. The method of claim 1, further comprising actuating, by the one or more processors, at least one of the two or more controllable regions of the garment, by controlling one or more actuators to dynamically adjust the fit of the garment to the user.

6. The method of claim 1, further comprising performing a diagnostic function, by the one or more processors and based on the detected user's movement of the particular part of the user's body.

7. A garment, comprising:
two or more controllable regions of fabric;
one or more sensors configured to:
detect movement of a particular body part of a user of a plurality of users, wherein the particular body part is a part of the user's body enclosed within the garment; and
measure data that indicates the detected movement of the particular body part of the user's body; and
an electronic controller comprising one or more processors that is in communication with the two or more controllable regions of fabric and the one or more sensors configured to:
determine, based on the measured data, an activity classification that indicates a future movement of the particular body part of the user's body, wherein:
the activity classification comprises inputting, to a machine learning model trained to classify the detected movement into an activity type, the measured data, and
the machine learning model is trained specifically for the user and movement characteristics of the user that includes at least one of: an amount of energy expenditure, an impact force, or a range of motion;
identify, based on the determined activity classification that indicates the future movement of the particular part body part of the user's body and by the one or more processors, a support configuration of the garment; and
dynamically adjust at least one of a tension and a stiffness of at least one of the two or more controllable regions of fabric to provide the identified support configuration of the garment.

8. The garment of claim 7, wherein dynamically adjusting at least one of the tension and the stiffness of at least one of the two or more controllable regions of fabric comprises controlling one or more actuators based on the determined activity classification, and
wherein each of the two or more controllable regions of fabric are made of non-stretch fabric.

9. The garment of claim 7, wherein determining the activity classification comprises inputting, to the machine learning trained to classify detected movement into an activity, the measured data that indicates the detected movement.

10. The garment of claim 9, the sensors further configured to:
record data that indicates detected movement of the particular part of the user's body in response to the dynamic adjustment of at least one of the tension and the stiffness of at least one of the two or more controllable regions of fabric; and
wherein the electronic controller is further configured to update, based on the recorded data, the machine learning model.

11. The garment of claim 7, the electronic controller further configured to:
actuate at least one of the two or more controllable regions of fabric, by controlling one or more actuators to dynamically adjust the fit of the garment to the user.

12. The garment of claim 7, the electronic controller further configured to:
perform a diagnostic function based on the detected user's movement of the particular part of the user's body.

13. A computer-readable storage device storing instructions that when executed by one or more processors cause the one or more processors to perform operations comprising:
detecting, by one or more sensors integrated with a garment having two or more controllable regions, movement of a particular body part of a user of a plurality of users, wherein the particular body part is a part of the user's body enclosed within the garment;
measuring, by the one or more sensors, data that indicates the detected movement of the particular body part of the user's body;
determining, based on the measured data and, an activity classification that indicates a future movement of the particular body part of the user's body, wherein:
the activity classification comprises inputting, to a machine learning model trained to classify the detected movement into an activity type, the measured data, and
the machine learning model is trained specifically for the user and movement characteristics of the user that includes at least one of: an amount of energy expenditure, an impact force, or a range of motion;
identifying, based on the determined activity classification that indicates the future movement of the particular body part of the user's body, a support configuration of the garment; and
dynamically adjusting, at least one of a tension and a stiffness of at least one of the two or more controllable regions of the garment to provide the identified support configuration of the garment.

14. The computer-readable storage device of claim 13, wherein dynamically adjusting at least one of the tension and the stiffness of at least one of the two or more controllable regions of the garment, comprises controlling one or more actuators based on the determined activity classification.

15. The computer-readable storage device of claim 13, wherein determining the activity classification comprises inputting, to the machine learning model trained to classify detected movement into an activity, the measured data that indicates the detected movement.

16. The computer-readable storage device of claim 15, further comprising:
  recording, by the one or more sensors, data that indicates detected movement of the particular part of the user's body in response to the dynamic adjustment of at least one of the tension and the stiffness of at least one of the two or more controllable regions of the garment; and
  updating, based on the recorded data, the machine learning model.

17. The computer-readable storage device of claim 13, further comprising actuating, at least one of the two or more controllable regions of the garment, by controlling one or more actuators to dynamically adjust the fit of the garment to the user.

* * * * *